(12) United States Patent
Rothenberger et al.

(10) Patent No.: US 8,865,963 B2
(45) Date of Patent: Oct. 21, 2014

(54) ABSORBENT ARTICLE HAVING VISIBLE INDICIA AND METHOD OF MAKING THE SAME

(76) Inventors: Ron Rothenberger, Collegeville, PA (US); Loida Guzman Reyes, Philadelphia, PA (US); Brian McGinty, Collegeville, PA (US)

( * ) Notice: Subject to any disclaimer, the term of this patent is extended or adjusted under 35 U.S.C. 154(b) by 1119 days.

(21) Appl. No.: 12/050,384

(22) Filed: Mar. 18, 2008

(65) Prior Publication Data

US 2009/0240221 A1 Sep. 24, 2009

(51) Int. Cl.
*A61F 13/20* (2006.01)
*A61F 13/15* (2006.01)
*A61F 13/514* (2006.01)

(52) U.S. Cl.
CPC ..... *A61F 13/15699* (2013.01); *A61F 13/51496* (2013.01); *A61F 2013/15243* (2013.01); *A61F 13/51464* (2013.01); *A61F 13/51484* (2013.01); *A61F 13/51478* (2013.01)
USPC .. 604/365; 604/367; 604/385.22; 604/385.01

(58) Field of Classification Search
CPC ................................ A61F 13/20; A61F 13/15
USPC ........... 604/365, 385.01, 385.22–385.31, 367
See application file for complete search history.

(56) References Cited

U.S. PATENT DOCUMENTS

| | | | |
|---|---|---|---|
| 4,048,736 A | | 9/1977 | Castleman et al. |
| 6,554,815 B1 * | | 4/2003 | Umebayashi ............ 604/385.27 |
| 6,558,499 B1 * | | 5/2003 | Pargass et al. ................ 156/250 |
| 7,217,261 B2 * | | 5/2007 | Otsubo et al. ............ 604/385.29 |
| 7,530,972 B2 * | | 5/2009 | Ando et al. ............... 604/385.27 |
| 2002/0046802 A1 * | | 4/2002 | Tachibana et al. ............ 156/209 |
| 2003/0135189 A1 * | | 7/2003 | Umebayashi ............ 604/385.27 |
| 2004/0016500 A1 * | | 1/2004 | Tachibana et al. ............ 156/179 |
| 2004/0030317 A1 * | | 2/2004 | Torigoshi ................. 604/385.27 |
| 2004/0167494 A1 * | | 8/2004 | Otsubo .................... 604/385.27 |
| 2004/0186453 A1 * | | 9/2004 | Shimada et al. ......... 604/385.27 |

(Continued)

FOREIGN PATENT DOCUMENTS

WO 9408799 A1 4/1994

OTHER PUBLICATIONS

Definitions of "resin", "synthetic resin" and "polyolefin", Hawley's Condensed Chemical Dictionary, 14th ed., 2002.*

(Continued)

*Primary Examiner* — Tatyana Zalukaeva
*Assistant Examiner* — Benedict L Hanrahan
(74) *Attorney, Agent, or Firm* — Amster, Rothstein & Ebenstein LLP (57) ABSTRACT

A multiple layer laminate and method of manufacturing the same having visible indicia for use in an absorbent article includes a first outer layer, a second outer layer, an elastomeric film interposed between said first outer layer and said second outer layer and a non-elastomeric appliqué having the indicia. The non-elastomeric appliqué is interposed between the elastomeric film and the first outer layer or between the elastomeric film and the second outer layer. The non-elastomeric appliqué is coupled to the elastomeric film in a stretched condition such that the non-elastomeric appliqué limits the retraction of the elastomeric film from the stretched condition in a location where the non-elastomeric appliqué is coupled to the elastomeric film, wherein the indicia is positioned to be visible through the first outer layer, the second outer layer or the first and the second outer layers.

26 Claims, 8 Drawing Sheets

(56) References Cited

U.S. PATENT DOCUMENTS

| | | | |
|---|---|---|---|
| 2004/0230171 A1* | 11/2004 | Ando et al. | 604/355 |
| 2006/0130964 A1* | 6/2006 | McCabe | 156/250 |
| 2006/0212010 A1* | 9/2006 | Roe et al. | 604/361 |
| 2007/0005035 A1 | 1/2007 | Snauwaert et al. | |
| 2007/0032766 A1 | 2/2007 | Liu et al. | |
| 2007/0208316 A1* | 9/2007 | Nakahata et al. | 604/385.02 |
| 2007/0265591 A1* | 11/2007 | Loritz et al. | 604/361 |
| 2007/0287975 A1* | 12/2007 | Fujimoto et al. | 604/385.3 |
| 2008/0132871 A1* | 6/2008 | Otsubo | 604/385.23 |

OTHER PUBLICATIONS

International Search Report of PCT/US2009/037521 dated May 20, 2009.

Written Opinion of PCT/US2009/037521 dated May 20, 2009.

\* cited by examiner

ABSORBENT ARTICLE HAVING VISIBLE INDICIA AND METHOD OF MAKING THE SAME

FIELD OF THE INVENTION

This invention relates generally to a multiple layer laminate having a visible indicia for use in absorbent articles, such as adult incontinence garments, feminine hygiene pads and the like, such as disposable underwear, adult and youth briefs, and training pants for children. More specifically, this invention relates to a multiple layer laminate having a visible indicia for use in an absorbent article that can be manufactured efficiently and economically, which exhibits good fit and comfort.

BACKGROUND OF THE INVENTION

Absorbent articles such as disposable diapers, training pants, adult incontinence garments and the like are known, their major function being to absorb and contain body exudates. Such articles are thus intended to prevent the soiling, wetting, or other contamination of clothing or other articles, such as bedding, that come into contact with the wearer. In the case of disposable absorbent articles, a variety of designs and manufacturing techniques have been developed to maximize performance and comfort to the wearer, as well as to obtain an absorbent article having a visible indicia that is aesthetically pleasing to the wearer. However, many of the current designs and manufacturing methods have been unable to achieve an optimum balance between these desirable, yet often diverging goals. While many developments have been made in the art of disposable absorbent undergarments, there remains a need for further improvements in both design and manufacturing.

SUMMARY OF THE INVENTION

In one aspect, the invention provides a multiple layer laminate having visible indicia for use in an absorbent article. The multiple layer laminate comprises a first outer layer, a second outer layer and an elastomeric film interposed between the first outer layer and the second outer layer. A non-elastomeric appliqué having the indicia is interposed between the elastomeric film and the first outer layer or between the elastomeric film and the second outer layer. The non-elastomeric appliqué is coupled to the elastomeric film in a stretched condition such that the appliqué limits the retraction of the elastomeric film from the stretched condition in a location where the appliqué is coupled to the elastomeric film, wherein the indicia is positioned to be visible through the first outer layer, the second outer layer or the first and the second outer layers.

In another aspect, the invention provides an absorbent article having visible indicia. The absorbent article comprises a multiple layer chassis, at least a portion of which includes a first outer layer, a second outer layer, an elastomeric film interposed between the first outer layer and the second outer layer and a non-elastomeric appliqué having the indicia. The non-elastomeric appliqué is interposed between the elastomeric film and the first outer layer or between the elastomeric film and the second outer layer. The non-elastomeric appliqué is coupled to the elastomeric film from a stretched condition such that the appliqué limits the retraction of the elastomeric film from the stretched condition in a location where the appliqué is coupled to the elastomeric film, wherein the indicia is positioned to be visible through the first outer layer, the second outer layer or the first and the second outer layers.

In a yet another aspect, the invention provides an absorbent article having visible indicia. The absorbent article comprises a front panel, a rear panel and a crotch panel extending between the front panel and the rear panel. The crotch panel is associated with an absorbent core wherein edges of the front panel are connected to edges of the rear panel to define a waist opening. The front panel or the rear panel comprises a multiple layer having a first outer layer, a second outer layer, an elastomeric film interposed between the first outer layer and the second outer layer and a non-elastomeric appliqué having the indicia. The non-elastomeric appliqué is interposed between the elastomeric film and the first outer layer or between the elastomeric film and the second outer layer. The non-elastomeric film is coupled to the elastomeric film. The indicia is positioned to be visible through the first outer layer or the second outer layer.

In still yet another aspect, the invention provides a method of manufacturing a multiple layer laminate having visible indicia for use in an absorbent article. The method of manufacturing comprises the step of interposing an elastomeric film in a stretched condition between a first outer layer and a second outer layer. A further step of the method includes interposing a non-elastomeric appliqué having the visible indicia between the elastomeric film and the first outer layer or between the elastomeric film and the second outer layer to form the multiple layer laminate such that the indicia is visible through the first outer layer, the second outer layer or the first and the second outer layers. Another step includes coupling together the non-elastomeric appliqué to the elastomeric film thereby limiting the retraction of the elastomeric film from the stretched condition in a location where the non-elastomeric appliqué and the elastomeric film are coupled together.

In a further aspect, the invention provides a method of manufacturing a multiple layer laminate having visible indicia for use in an absorbent article. The method comprises the step of elongating an elastomeric film. The method further includes positioning a non-elastomeric appliqué having the indicia adjacent a first nonwoven web, positioning a first surface of the elastomeric film adjacent the appliqué to sandwich the appliqué between the elastomeric film and the first nonwoven web, and positioning a second nonwoven web adjacent a second surface of the elastomeric film. The method also includes the step of bonding the elastomeric film, the appliqué and the first and second nonwoven webs to one another to form the multiple layer laminate.

BRIEF DESCRIPTION OF THE DRAWINGS

The invention is best understood from the following detailed description when read in connection with the accompanying drawing. It is emphasized that, according to common practice, the various features of the drawing are not rendered to scale. On the contrary, the dimensions of the various features are arbitrarily expanded or reduced for clarity. Included in the drawing are the following figures, in which like reference numerals refer to similar features in the respective Figures.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

It is desirable in the art of absorbent articles, such as disposable underwear, briefs and training pants, to produce an absorbent article having visible indicia on at least a portion of the absorbent article to make the article more aesthetically pleasing to the wearer, without sacrificing overall performance of the absorbent article. For example, in some conventional absorbent articles, typical outer covers comprise a nonwoven material or the like. Generally, such material is less desirable or less suitable than other surfaces, such as a thermoplastic material surfaces, for providing a surface for printing or including indicia thereon, because it is difficult to print on such fibrous surfaces. Likewise, it is possible to provide an indicia-bearing substrate positioned on a portion of the outside of the nonwoven outer cover. However, including such indicia-bearing substrates results in the absorbent article being less comfortable for the wearer. This is because materials most suitable for printing indicia thereon are generally materials that are not as soft as nonwoven material and are more likely to irritate the skin of the wearer.

The present invention provides an improved absorbent article by providing a multiple layer laminate for use in an absorbent article that is aesthetically pleasing, and also one that maximizes performance and comfort to the wearer of the absorbent article. In one aspect, the invention provides a multiple layer laminate having visible indicia for use in an absorbent article. The multiple layer laminate comprises a first outer layer and a second outer layer. Further, the multiple layer laminate provides an elastomeric film that is interposed between the first outer layer and second outer layer. The multiple layer laminate also includes a non-elastomeric appliqué having the indicia, the non-elastomeric appliqué being interposed between the elastomeric film and the first outer layer. Alternatively, the absorbent article provides a non-elastomeric appliqué between the elastomeric film and the second outer layer. The non-elastomeric appliqué is coupled to the elastomeric film in a stretched condition such that the appliqué limits the retraction of the elastomeric film from the stretched condition. Further, the indicia is positioned to be visible through the first outer layer, the second outer layer or the first and the second outer layers.

By coupling the non-elastomeric appliqué in this way, preferably with ultrasonic bonds, to the elongated elastomeric film, the appliqué limits the ability of the elastomeric film to substantially retract to its un-elongated condition. In an exemplary embodiment, the appliqué is of a gauge or thickness, or has a column strength, such that the retractive force of the elastomeric film does not cause "neck-down" of the appliqué. As used herein, the term "neck-down," refers to the gathering of the material that results in bending, bunching, folding or the like, of the material as a result of the retractive force of the elastomeric film from its stretched condition that is applied to the appliqué.

In another exemplary embodiment, in which the appliqué is of a lesser gauge or thickness, or has a lesser column strength, the retractive force causes a predetermined amount of neck-down of the appliqué. Preferably, the percentage of neck-down of the appliqué is in the range of about 0% to about 40%, when the elastomeric film is retracted from the stretched condition. More preferably, the percentage of neck-down of the appliqué is in the range of about 10% to about 30%. The percentage of neck-down is based on the length of the appliqué when it is laid flat as compared to the length of the appliqué when the retractive force of the elastomeric film acts on the appliqué. In other words, the percentage of neck-down is the reduction in the footprint of the appliqué both before and after the retractive force of the elastomeric film acts on the appliqué.

In embodiments of the invention where neck-down occurs, in order to compensate for the neck-down of the appliqué, the indicia on the appliqué will be printed with some distortion, for example, by being printed in a widened manner. For example, ovals may be printed on the appliqué that will be viewed as circles once the elastomeric film retracts causing the appliqué to neck-down. By printing in a distorted manner, when the retractive force of the elastomeric film causes the appliqué to neck-down, the indicia will also retract and appear without, or with minimal, distortion. The amount of distortion applied to the indicia is determined based on the amount of neck-down of the appliqué. For example, a 10% distortion in the direction of the neck-down would be applied for an appliqué designed to provide a neck-down of 10%. The ratio would be approximately a 1:1 ratio. Accordingly, the amount of distortion applied to the indicia may be about 0% to about 40%; preferably about 10% to about 30%, though other ranges are contemplated as well.

It is recognized that in embodiments in which the appliqué is of a gauge or thickness, or has a column strength such that the appliqué has a neck-down of about 0%, the appliqué may be too stiff to maximize comfort for the wearer. In this instance, however, the embodiment provides the advantage that the indicia on the appliqué does not need to be distorted, as the appliqué will have minimal, if any, neck-down.

Figure 1:
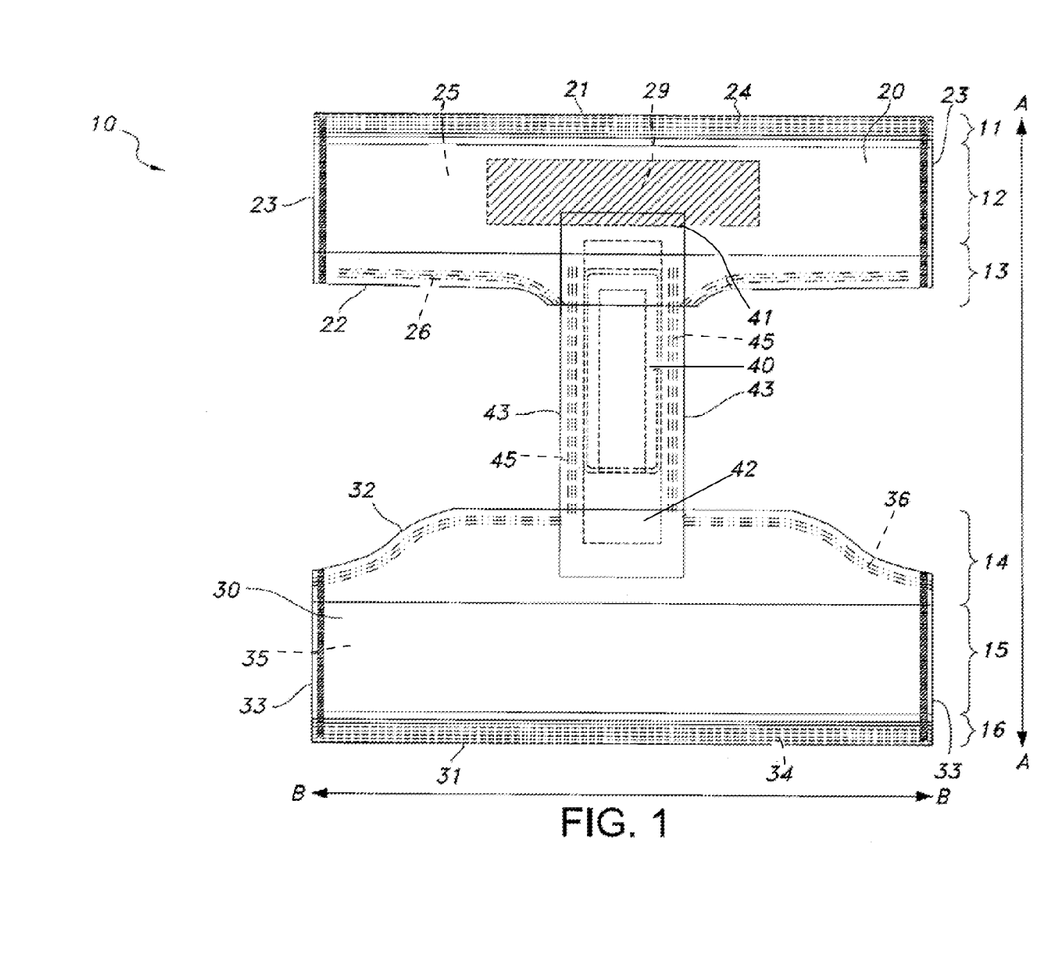
FIG. 1 is a plan view of an exemplary embodiment of an absorbent article in a partially unassembled, flat state in which the body-side surface of the absorbent article faces the viewer.

Referring generally to the drawing, FIG. 1 illustrates an exemplary embodiment of a type of an absorbent article that may be configured to include the multiple layer laminate of the invention. An absorbent article 10 is shown in a partially unassembled, flat state, the body-side surface of the absorbent article 10 facing the viewer. The arrows A-A generally indicate a longitudinal dimension, or length, of the absorbent article 10 in the partially unassembled state. This longitudinal orientation corresponds to the longitudinal orientation of the crotch panel 40 of the absorbent article 10. Also, the arrows B-B generally indicate the width dimension of the absorbent article 10 in the partially unassembled state. The direction B-B also corresponds to the machine direction optionally used to make at least some of the components of the absorbent article 10. More specifically, front panel 20 and rear panel 30 of the absorbent article 10 (described below) are optionally formed from a continuous web or continuous webs that are directed along a machine direction parallel to B-B.

Figure 2:
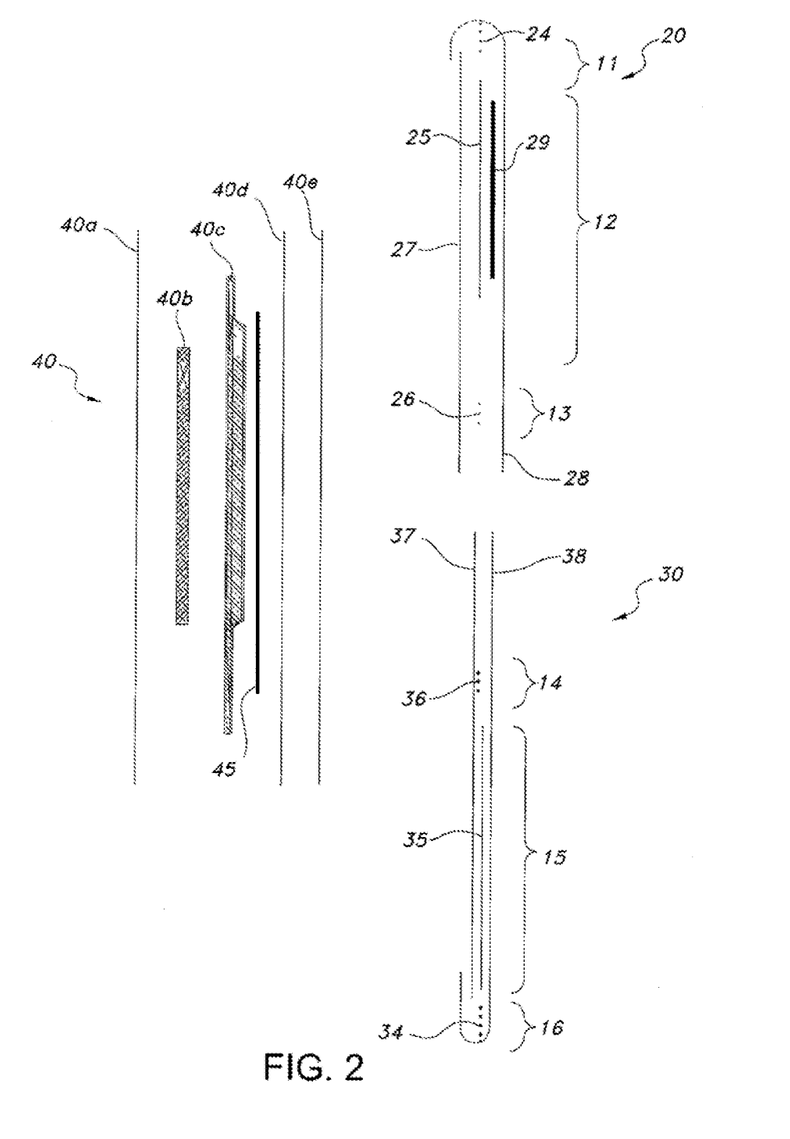
FIG. 2 is a partial side cross-sectional view of the front, rear and crotch panels of the absorbent article as shown in FIG. 1.
Figure 3:
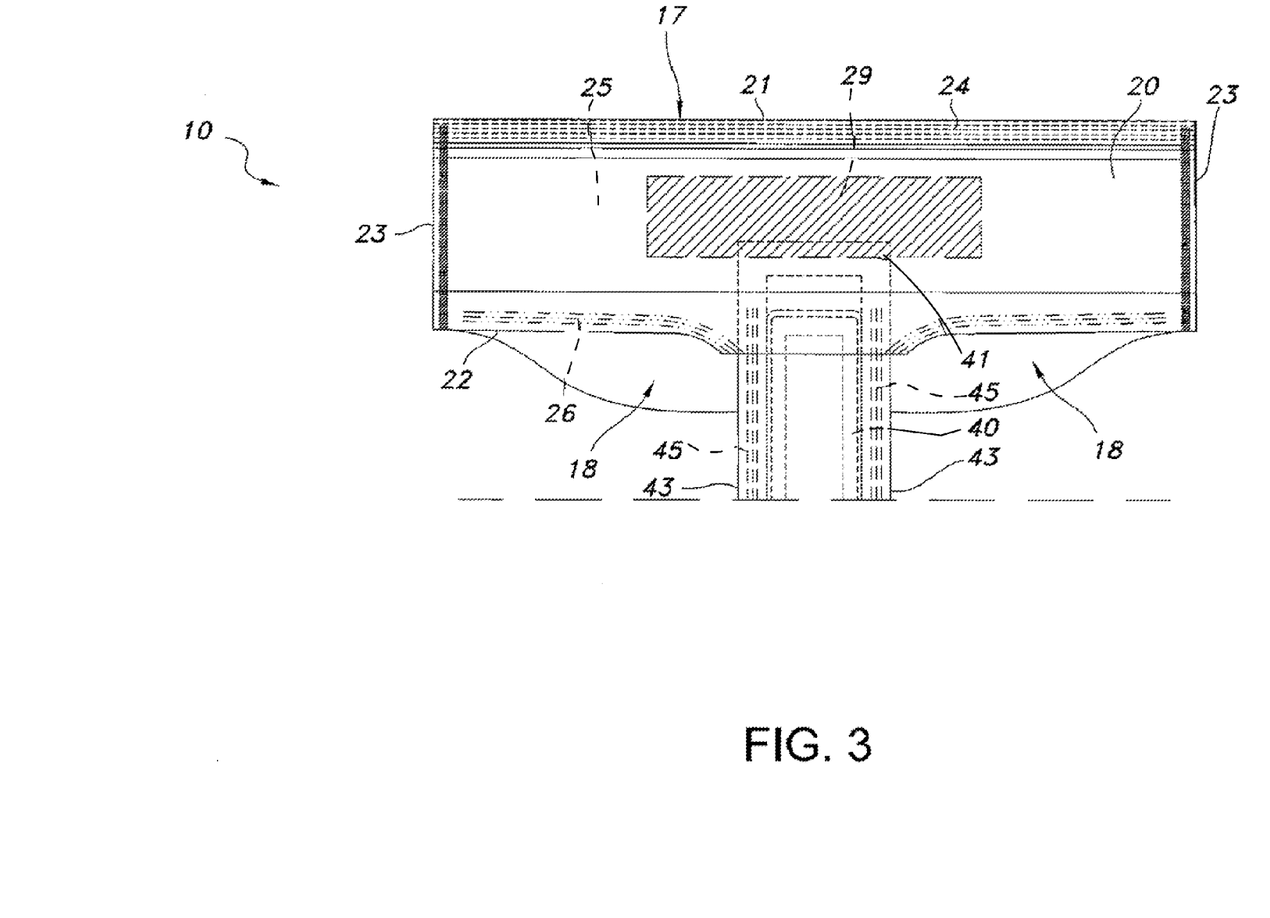
FIG. 3 is a front view of the absorbent article of FIG. 1 in its assembled state.

With reference to FIG. 1, the absorbent article 10 comprises a front panel 20, a rear panel 30, and a crotch panel 40, the crotch panel 40 extending between the front panel 20 and the rear panel 30. The crotch panel is associated with absorbent core 40c, as shown in FIG. 2. Fully assembled, as shown in FIG. 3, the absorbent article 10 forms an assembled pants-shaped undergarment. As shown in its assembled configuration, edges 23 of the front panel 20 and edges 33 of the rear panel 30 are connected to define a waist opening at 17. In such an embodiment, the waist elastics 24, 34 extend to cover the circumference of the product. In other words, when fully assembled, the absorbent article includes waist elastics 24, 34 attached from end to end to form waist opening 17. Further, the absorbent article 10 includes leg openings 18 located on opposing sides of the crotch panel 40.

As shown in FIG. 1, in an exemplary configuration of the absorbent article, the front panel 20 includes a waist end 21 along its length, a crotch end 22 spaced apart in the width direction from the waist end 21, and two substantially straight sides 23 that extend between the waist end 21 and the crotch end 22. The front panel 20, as shown in FIG. 1, includes a waist area 11, a belly area 12, and a leg/thigh area 13. Also as shown in FIG. 1, front panel 20 includes an appliqué 29 included therein.

Similar to the front panel 20, the rear panel 30 of the absorbent article 10, according to the exemplary embodiment of FIG. 1, includes a waist end 31 along a length direction, a crotch end 32 spaced apart in the width direction from the waist end 31, and two substantially straight sides 33 extending between the waist end 31 and the crotch end 32. The rear panel 30 is separated from the front panel 20 in the width direction by a gap between the two panels which is bridged by crotch panel 40. The rear panel 30, as shown in FIG. 1, includes waist area 16, mid-section 15, and leg/thigh area 14. For simplicity, mid-section 15 will hereinafter be referred to as belly area 15.

Also illustrated in FIG. 1, crotch panel 40 has a front end portion 41, a rear end portion 42 longitudinally spaced from the front end 41, and two sides 43 extending between the front end portion 41 and the rear end portion 42. The front end portion 41 is fixed to front panel 20 and the rear end portion 42 is fixed to rear panel 30 thereby bridging the gap between the crotch end 22 of the front panel 20 and the crotch end 32 of the rear panel 30. Further, the crotch panel 40, as shown in FIG. 1, has a generally rectangular shape. Optionally, the crotch panel 40 may also have other shapes, for example an oval shape or any other straight-sided or curved shape.

Referring to FIG. 2, which is a side cross-sectional view of absorbent article 10 of FIG. 1, the absorbent article is shown having a front panel 20, in which the front panel 20 comprises a multiple layer subassembly. The multiple layer subassembly of the front panel 20 comprises an outer layer 28 and an inner layer 27. Interposed between the outer layer 28 and the inner layer 27, the subassembly includes waist elastics 24, belly elastic 25 and leg/thigh elastics 26. The multiple layer subassembly also includes an appliqué 29 interposed between the belly elastics 25 and the outer layer 28. As shown in FIG. 1, the indicia, indicated by the diagonal lines, is visible through the outer layer 28. Referring again to FIG. 2, outer layer 28 is folded over waist elastics 24 and the inner layer 27 in the waist area 11. It should be noted that although layer 27 is called the "inner" layer in this embodiment for simplicity, the body-side of layer 27 is an external layer of the subassembly, and may also be referred to as an "outer" layer of the front panel 20 (in addition to outer layer 28).

In the exemplary embodiment shown in FIG. 2, the rear panel 30 also comprises a multiple layer subassembly. The subassembly of rear panel 30 comprises an outer layer 38 and an inner layer 37. Interposed between the outer layer 38 and the inner layer 37, the subassembly includes waist elastics 34, belly elastics 35 and leg/thigh elastics 36. As shown in FIG. 3, outer layer 38 is folded over waist elastics 34 and the inner layer 37 in the waist area 16. It should be noted here as well that, similar to the inner layer 27 of front panel 20, the "inner" layer 37 of rear panel 30 may also be referred to as an outer layer (in addition to the outer layer 38).

Exemplary material forming the front 20 and rear 30 panels of an absorbent article of an exemplary embodiment of the invention, including the rear panel inner layer 37 and outer layer 38 and front panel inner layer 27 and outer layer 28, as shown in FIG. 2, can be any suitable material used in disposable absorbent articles. Such materials suitable for use in the present invention are described, for example, in U.S. patent application Ser. Nos. 10/617,218, filed on Jul. 10, 2003, Ser. No. 11/236,994 filed on Sep. 28, 2005 and Ser. Nos. 11/904,467, 11/904,468, and 11/904,493, all of which were filed on Sep. 27, 2007, each of which applications are incorporated by reference in their entireties herein.

Interposed between the front and rear panel outer layers 28, 38 and inner layers 27, 37, respectively, the absorbent article 10 includes waist areas 11, 16, belly areas 12, 15, and leg/thigh areas 13, 14. The waist areas 11, 16 include waist elastics 24, 34, such as elastic strands, threads or filaments. The belly areas 12, 15 include belly elastics 25, 35, shown as elastomeric film. Optionally, the belly areas 12, 15 may be uni-directionally stretchable in a direction across a wearer's belly. And the leg/thigh areas 13, 14 include leg/thigh elastics 26, 36, which include elastic strands, threads or filaments. Optionally, the waist elastics 24, 34 and/or the leg/thigh elastics can be elastomeric film in place of the elastic threads or filaments.

Suitable elastomeric films that may be used in the present invention preferably include bidirectional film manufactured by Pliant Corp. Optionally, the elastomeric film has an elongation of about 80% to about 400%. Preferably, the elongation of the elastomeric film is about 300%. Suitable elastic threads or filaments that may be used in the present invention include, for example, the product spandex, sold under the trademarks LYCRA (manufactured by INVISTA) or CREORA (manufactured by Hyosung, Inc.).

As shown in FIG. 2, in the front panel 20 and interposed between the elastomeric film 25 and the outer layer 28, the absorbent article 10 includes non-elastomeric appliqué 29. The non-elastomeric appliqué 29 has an indicia thereon, or optionally included therein, which is visible through the outer layer 28. The indicia can include a non-elastomeric film having a sewn, embroidered or pasted material on the non-elastomeric film. Alternatively, the indicia can include an art graphic or other design printed or otherwise incorporated on a non-elastomeric film. For example, the graphic design can include a wide variety of shapes and characters aesthetically pleasing to wearers, such as cartoon characters for children. Suitable non-elastomeric films for use as an appliqué in the present invention can include thermoplastic film material, such as polypropylene or polyethylene. Although the appliqué is made of a non-elastomeric film material, optionally, the indicia, as noted above may be provided on the non-elastomeric film in a distorted manner to compensate for neck-down of the non-elastomeric film.

In an embodiment of the invention such as shown in FIG. 2, the non-elastomeric appliqué 29, being interposed between the elastomeric film 25 and the outer layer 28, is coupled to the elastomeric film 25, which is in an elongated, or stretched, condition. The appliqué 29 and the elastomeric film 25, along with the inner and outer layers 27 and 28, are coupled together such that the retraction of the elastomeric film is limited when the elastomeric film is relaxed, or allowed to return to its un-elongated, or pre-stretched, condition. Preferably, the elastomeric film 25, non-elastomeric appliqué 29 and the inner and outer layers 27 and 28, respectively, are coupled together with ultrasonic bonds. The ultrasonic bonding of the belly areas 12, 15 result in a multilayer subassembly having a more cotton-like, or underwear-like, look and feel. As an alternative to ultrasonic bonds, the bonds may be applied using other attachment means or mechanical methods, such as heat, pressure, embossing, or other mechanical methods.

The crotch panel 40 an exemplary embodiment of the absorbent article 10 can be configured as shown in FIG. 2. This embodiment includes a multilayer absorbent subassembly having a body-side (left side as shown in FIG. 2) and a garment-side (right side as shown in FIG. 2). As shown in the cross-sectional view, beginning from the body-side and continuing to the garment-side, the subassembly includes a cover 40a adjacent an acquisition/distribution layer (ADL) 40b, which is disposed adjacent an absorbent core 40c, which is adjacent a barrier layer 40d. Adjacent the body-side of the backsheet are disposed an insert outer cover, or backsheet, 40e. Crotch panel elastics 45 are disposed between cover 40a and barrier layer 40d.

In another embodiment, the ADL may comprise two separate layers including an acquisition layer and a distribution layer. While one exemplary embodiment of a crotch panel is shown for purposes of illustration, a wide variety of portions and composites are optionally used within the scope of this invention. Exemplary absorbent cores may include those for which the details of each of the layers and materials are as described in U.S. patent application Ser. No. 10/617,218, filed on Jul. 10, 2003, Ser. No. 11/236,994 filed on Sep. 28, 2005 and Ser. Nos. 11/904,467, 11/904,468, and 11/904,493, all of which were filed on Sep. 27, 2007, each of which applications are incorporated by reference in their entireties herein.

In another aspect, an exemplary embodiment of the invention provides an absorbent article having visible indicia in which the absorbent article comprises a multiple layer chassis, as least a portion of which includes a first outer layer, a second outer layer, an elastomeric film interposed between the first outer layer and the second outer layer and a non-elastomeric appliqué interposed between the elastomeric film and the first outer layer, or between the elastomeric film and the second outer layer. The portion of the multiple layer chassis shown in FIG. 4 as front panel 120 can be included in an absorbent article, such as that shown as absorbent article 10 in FIG. 1. For example, the absorbent article 10 includes absorbent core 40c with the front panel 20, rear panel 30 and crotch panel 40, collectively shown as the multiple layer chassis, a portion of which is front panel 20, for example. The multiple layer chassis, however, may also be a portion of an absorbent article, such as a disposable underwear, an adult or children's brief, training pants, sanitary napkins, and the like.

Figure 4:
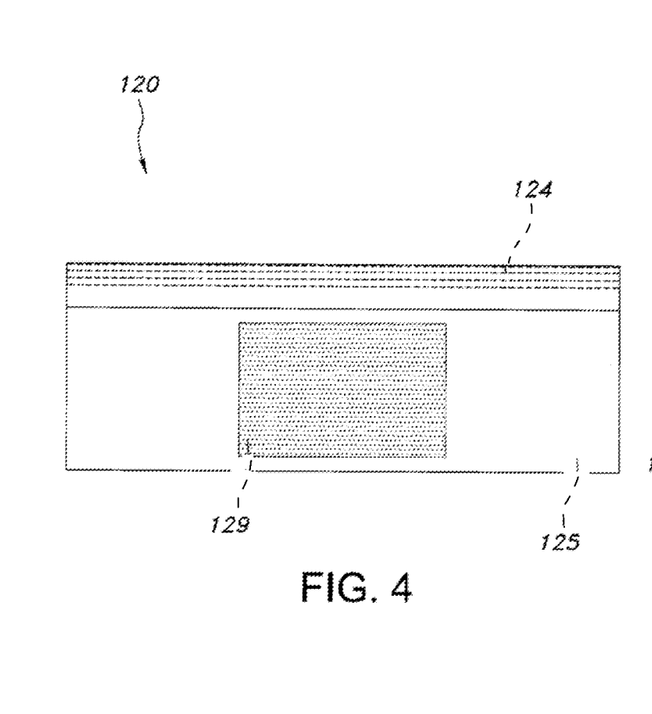
FIG. 4 is a plan view of another exemplary embodiment of the invention, including a portion of a multiple layer chassis of an absorbent article in which the body-side surface of the absorbent article faces the viewer.
Figures 5, 6:
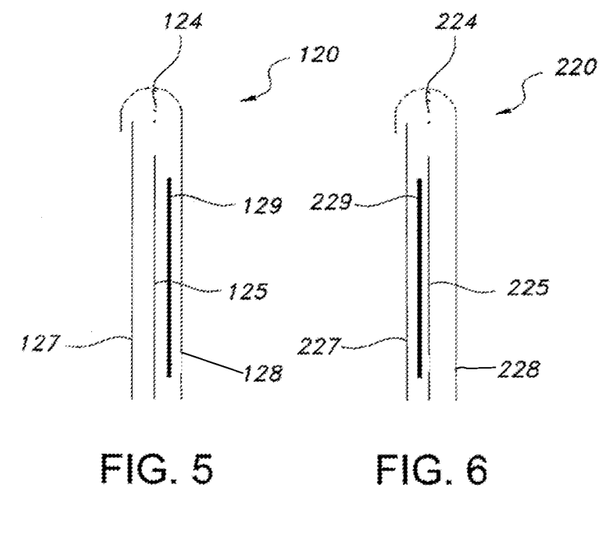
FIG. 5 is a partial side cross-sectional view of the absorbent article shown in FIG. 4.
FIG. 6 is a partial side cross-sectional view of another embodiment of the absorbent article of FIG. 4.

As shown in FIGS. 4 and 5, in an exemplary embodiment of this aspect, a portion of the multiple layer chassis includes a panel, shown as front panel 120, including a first outer layer 128, a second outer layer 127 and an elastomeric film 125 interposed between the first outer layer 128 and the second outer layer 127. The absorbent article further includes a non-elastomeric appliqué 129 which incorporates the indicia, represented by small dots, the appliqué 129 being interposed between the elastomeric film 125 and the first outer layer 128.

The non-elastomeric appliqué 129 is coupled to the elastomeric film 125 or to the first and/or second outer layer 127, 128, in which the elastomeric film 125 is in a stretched condition. The non-elastomeric appliqué 129 and the elastomeric film 125 are also preferably bonded to the first outer layer 128 and the second outer layer 127. When bonded, the elastomeric film 125 is allowed to relax. However, the retraction of the elastomeric film 125 is limited by the bonding of the non-elastomeric appliqué 129 to the elastomeric film 125 in the location where the non-elastomeric appliqué 129 is coupled to the elastomeric film 125. The tension provided by the bonds also causes the non-elastomeric appliqué 129 to neck-down when the retractive forces from the stretched condition of the elastomeric film 125 are strong enough to cause the non-elastomeric 129 appliqué to become bunched. For example, the non-elastomeric appliqué 125 may be designed so as to provide a neck-down of about 0% to about 40%. Neck-down may be decreased based on the thickness of the appliqué or the particular rigidness of the thermoplastic materials from which it is made. The indicia is visible through the first outer layer 128. The indicia may also, optionally, be visible through the elastomeric film 125 and the second outer layer 127. Also, although shown in FIG. 4 as including waist elastics 124 interposed between the first outer layer 128 and the second outer layer 127, the front panel 220 may also be designed so as to not include waist elastics 124.

In an alternative embodiment, as shown in FIG. 6, the non-elastomeric appliqué 229 may be interposed between the elastomeric film 225 and the second outer layer 227. In this embodiment, the indicia of appliqué 229 is visible through the second outer layer 227. Optionally, the indicia of appliqué 229 is also visible through the elastomeric film 225 and first outer layer 228. In the embodiment shown in FIG. 6, the second outer layer may be disposed on the body-side of the wearer, such that the appliqué 229 is visible on the body-side of the front panel 220 through the second outer layer 227, instead of first outer layer 228. In this embodiment, the appliqué 129 may include an image thereon intended to be viewed only by the wearer. For example, the appliqué may include an image, such as one designating a size of the absorbent article, for example, "S", "M", "L" or "XL," representing the sizes small, medium, large and extra large. As another example, the indicia may also contain other information, such as the manufacturer or origin of the absorbent article, or may include a listing of the materials of construction of the absorbent article. Optionally, the front panel 220 may also include waist elastics 224, as shown in FIG. 6.

Figure 7A:
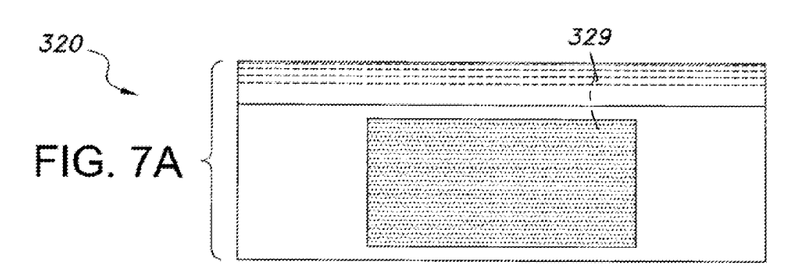
FIGS. 7A, 7B and 7C are plan views of additional exemplary embodiments of a portion of a multiple layer of an absorbent article illustrating optional exemplary configurations for an appliqué in which the body-side surface of the absorbent article faces the viewer.
Figure 7B:
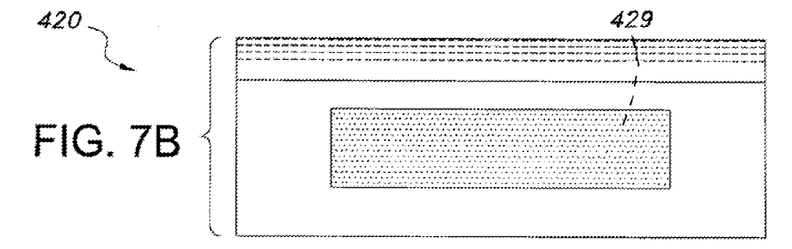
Figure 7C:
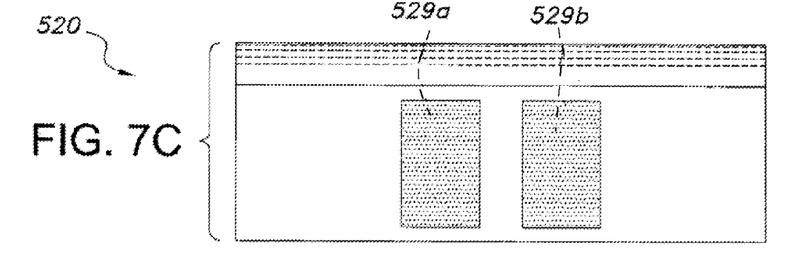

Referring to FIGS. 7A, 7B and 7C, the appliqué, shown as 329, 429, and 529a and 529b, of portions of multiple layer chassis 320, 420 and 520, respectively, can vary in size in both the length and width dimensions. In the exemplary embodiment of the appliqué shown in FIG. 7C, the invention may also include multiple appliqués, for example two spaced apart appliqués, such as 529A and 529B.

Figure 8:
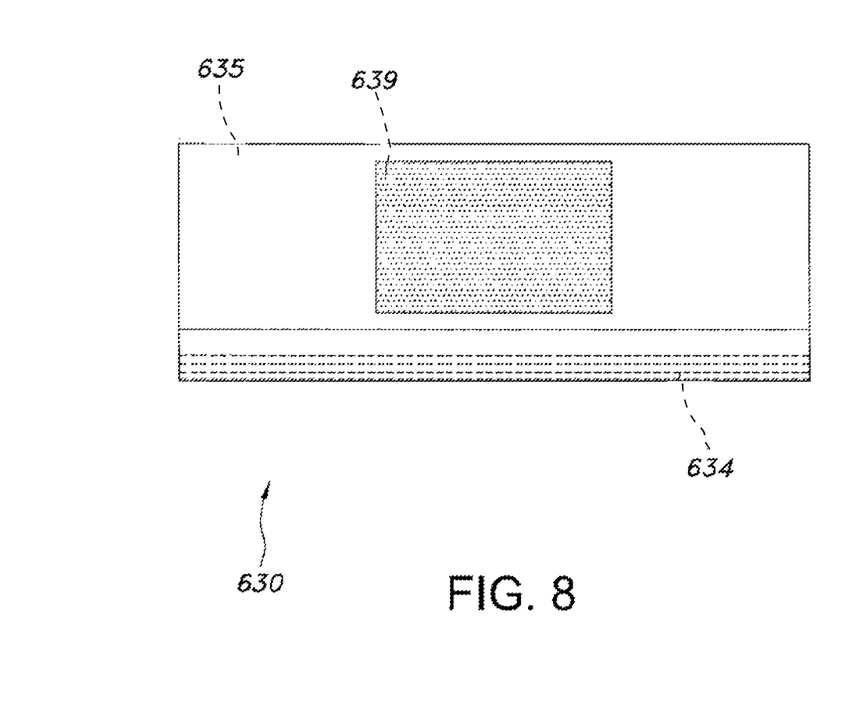
FIG. 8 is a plan view of an still another exemplary embodiment of invention, including another portion of a multiple layer chassis of an absorbent article in which the body-side surface of the absorbent article faces the viewer.
Figure 9:
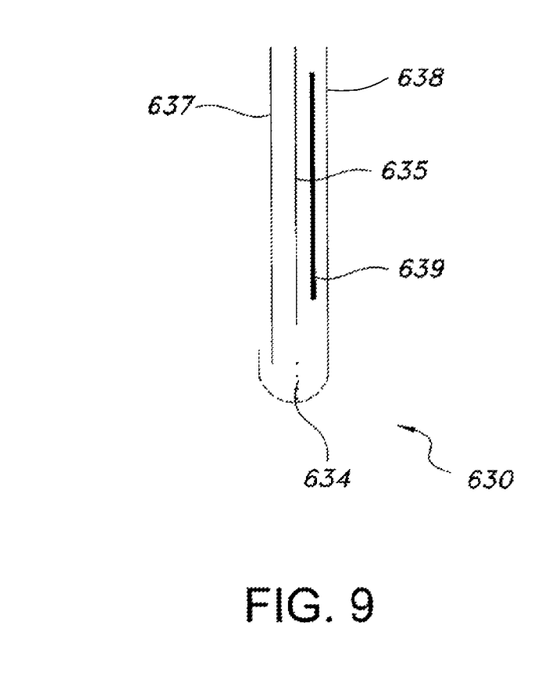
FIG. 9 is a partial side cross-sectional view of an embodiment of the absorbent article shown in FIG. 8.

Referring now to the embodiment shown in FIGS. 8 and 9, the illustrated portion of the multiple layer chassis comprises a rear panel, shown as 630. The portion of the multiple layer chassis includes a first outer layer 638, a second outer layer 637 and an elastomeric film 635 interposed between the first outer layer 638 and the second outer layer 637. The absorbent article further includes a non-elastomeric appliqué 639 which has the indicia, the appliqué 639 being interposed between the elastomeric film 635 and the first outer layer 638.

As with the front panel discussed previously, the non-elastomeric appliqué 639 of the rear panel 630 is coupled to the elastomeric film 635. The non-elastomeric appliqué 639 and the elastomeric film 635 are also preferably bonded to the first outer layer 638 and the second outer layer 637. The indicia is visible through the first outer layer 638. By coupling the elastomeric film 635 and the non-elastomeric appliqué 639 together, the ability of the elastomeric film 635 to return to its un-elongated or pre-stretched condition is limited. Further, the retractive force of the elastomeric film 635 that acts on the non-elastomeric appliqué 639 may cause the non-elastomeric appliqué to neck-down. Alternatively, similar to the embodiment shown in FIG. 6, in another alternative embodiment (not shown), the non-elastomeric appliqué 639 may be interposed between the second outer layer 637, such that the indicia is visible through the second outer layer 639. The rear panel may also include waist elastics 634 interposed between the outer layer 638 and the inner layer 637.

Optionally, in an embodiment (not shown) each of the front and rear panels of the absorbent article may contain a multiple layer subassembly, such that each of the front and rear panels include an appliqué. In such an embodiment, each of the front and rear panels would have an indicia incorporated in the appliqué that would be visible through either the body-side outer layers or the garment-side outer layers, or both.

Figure 10:
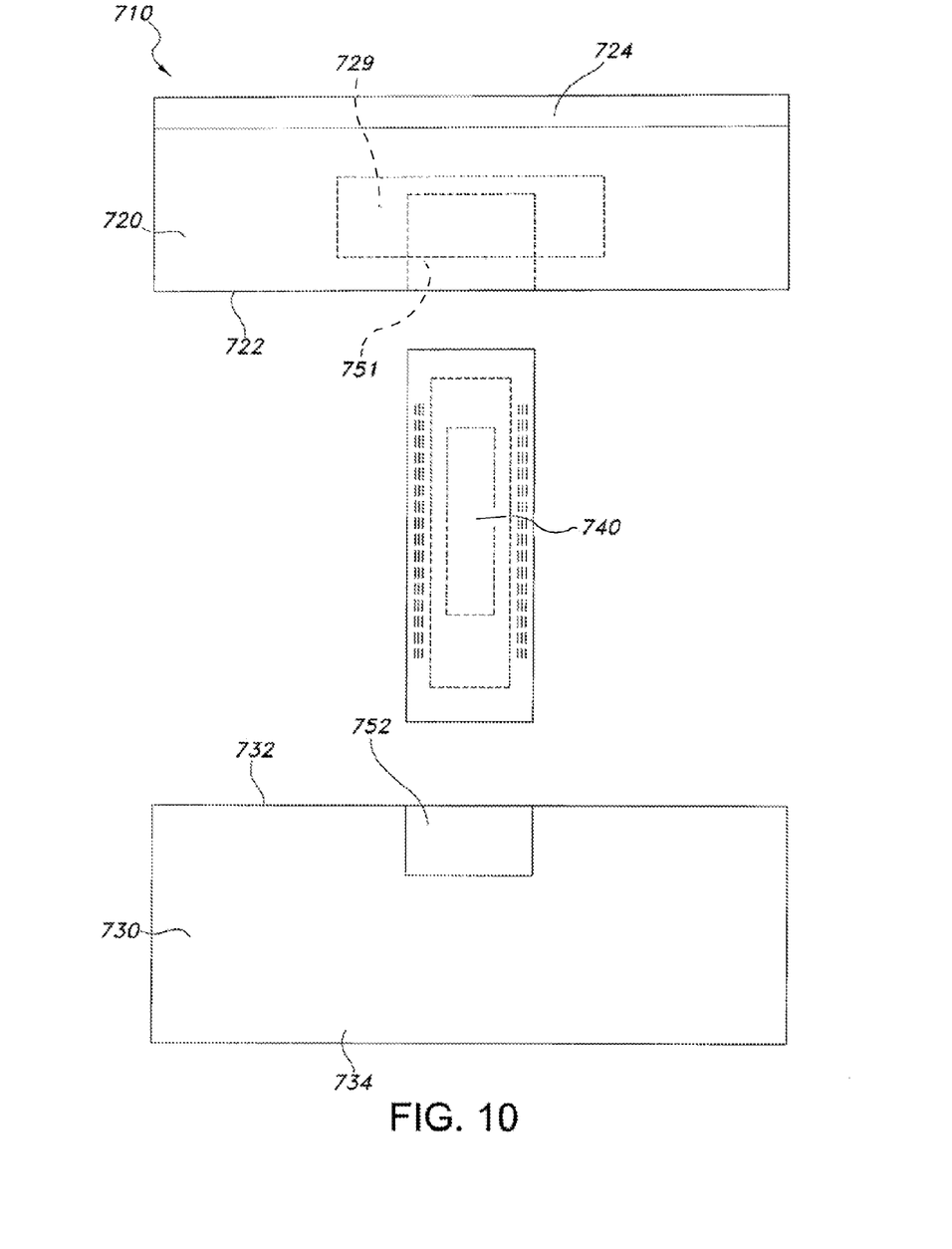
FIG. 10 is a simplified schematic plan view of yet another exemplary embodiment of an absorbent article illustrating an exemplary assembly of the crotch panel to the front and rear panels in which the body-side of the absorbent undergarment faces the viewer.

FIG. 10 illustrates another embodiment of the invention. As shown in FIG. 10, absorbent article 710 includes a front panel 720, a rear panel 730 spaced apart from the front panel 720 in the length direction and a crotch panel 740 therebetween. The front panel 720 includes appliqué 729 having indicia included therein. Each of the front panel 720 and rear panel 730 has a body-side and a garment-side. For illustration purposes, the body-side of absorbent article 710 shown in FIG. 10 faces the viewer. In at least one embodiment, the body-side of the crotch panel 740 has a front end fixed to the garment-side of the front panel 720 and a rear end that is fixed to the body-side of the rear panel 730.

This is exemplified by the schematic of FIG. 10, in which the area 751 defined by the dotted lines indicates the location where the crotch panel 740 is fixed to the garment-side of front panel 720 at crotch end 722. Likewise, the area 752 defined by solid lines indicates the location where the crotch panel 740 is fixed to the where crotch panel is fixed to the body-side of rear panel 730 at crotch end 732. The front 720 and rear 730 panels are shown as including optional waist elastics 724, 734.

It is also contemplated that the invention may also include graphic design or designs incorporated on the front end of the crotch panel, which may be attached to garment-side of the front panel 720, in addition to having an appliqué having indicia visible through the outer and/or inner layers of the front and/or rear panels. For example, the graphic design can include a wide variety of shapes and characters aesthetically pleasing to wearers, such as cartoon characters for children, as described in U.S. patent application Ser. Nos. 11/904,467, 11/904,468 and 11/904,493 all of which were filed on Sep. 27, 2007, and each of which is incorporated herein by reference.

Figure 11:
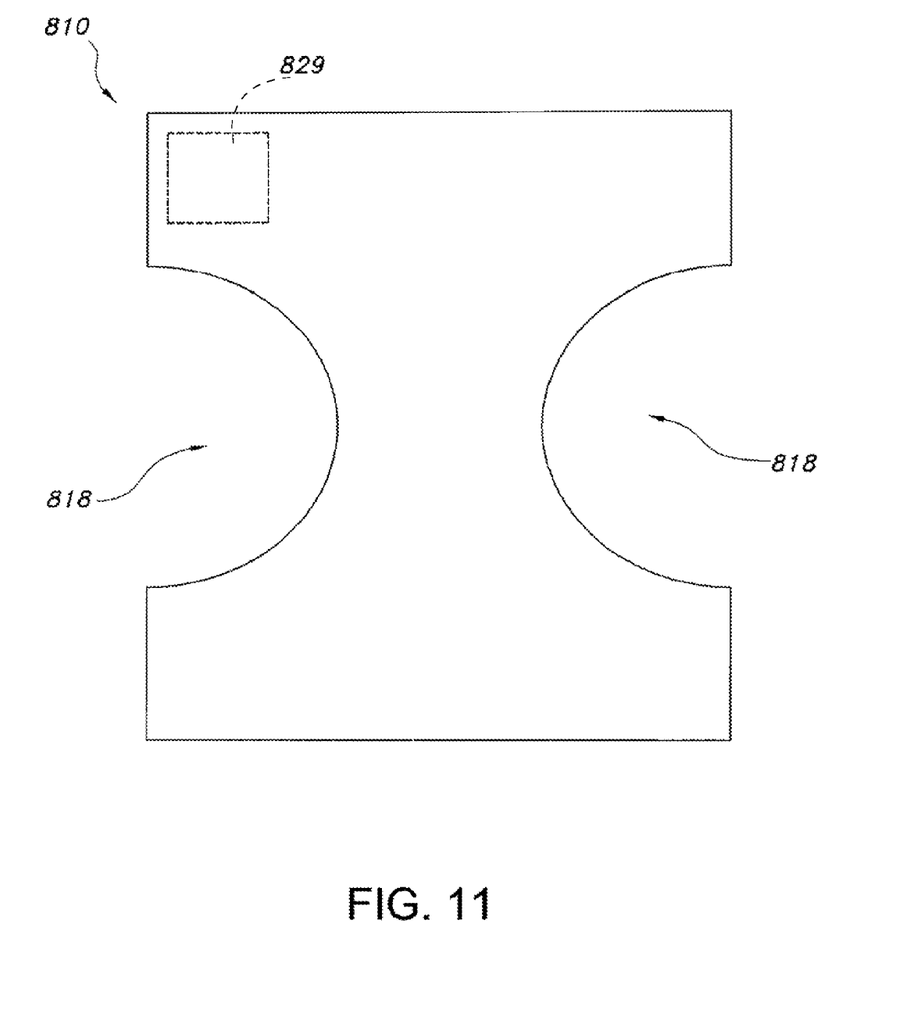
FIG. 11 is a schematic of an exemplary absorbent article having a visible indicia.

As shown in FIG. 11, the location of the appliqué may optionally be positioned in a side region of the absorbent article. FIG. 11 is a simplified schematic of an exemplary absorbent article, which can include any number of absorbent articles such as diapers, training pants, napkins, incontinence pads and the like. This illustration is not intended to be limited to any one type of absorbent article and is included to illustrate that the appliqué may be included in any number of locations in an absorbent article that includes the type of multiple layer laminate herein described. For example, FIG. 11 shows absorbent article 810, illustrated with leg openings 818, in which the appliqué is positioned in a side region or ear portion of the absorbent article. In another embodiment, the side region of FIG. 11 may also represent an exemplary embodiment of an absorbent article in which the appliqué is positioned in a fastening member portion of the absorbent article.

In another aspect, the present invention provides a method of manufacturing a multiple layer laminate having visible indicia for use an absorbent article. The method of manufacturing includes the steps of interposing an elastomeric film in a stretched condition between a first outer layer and a second outer layer and interposing a non-elastomeric appliqué having the visible indicia between the elastomeric film and the first outer layer. Alternatively, the method includes interposing a non-elastomeric appliqué in a stretched condition and having the visible indicia between the elastomeric film and the second outer layer. The method thus forms a multiple layer subassembly such that the indicia is visible through the first outer layer, the second outer layer or both of the first and the second outer layers. The method further includes the step of coupling together the non-elastomeric appliqué to the elastomeric film thereby limiting the retraction of the elastomeric film from the stretched condition in a location where the non-elastomeric appliqué and the elastomeric film are coupled together. Optionally, coupling the non-elastomeric appliqué to the elastomeric film may be performed by ultrasonically bonding the elastomeric film, the non-elastomeric appliqué, and the first and second outer layers together to form the multiple layer laminate.

Optionally, the method may further comprise distorting the indicia of the appliqué. As mentioned previously, the distortion may be included in order to compensate for the neck-down of the non-elastomeric appliqué resulting from the retractive forces of the elastomeric film. The method may thus further comprise the steps of relaxing the elastomeric film from the stretched condition. Additionally, the method may include limiting the neck down of the non-elastomeric appliqué to about 0% to about 40%. The method may also include the step of providing indicia on the appliqué in a distortion in a direction of the neck-down.

Optionally, the method of manufacturing may also include the step of associating the multiple layer laminate with an absorbent core. Absorbent cores for use in the present invention may include a number of absorbent cores suitable for use in diapers, training pants, napkins, incontinence pads and the like. The absorbent cores may include superabsorbent polymers and may comprise one or more layers of a number of liquid-absorbing materials of varying absorbent capacities depending on the use of the product.

In yet another aspect, the invention provides a method of manufacturing a multiple layer laminate having visible indicia for use in an absorbent article. The manufacturing method includes elongating an elastomeric film, as well as positioning a non-elastomeric appliqué adjacent a first nonwoven web and positioning a first surface of the elastomeric film adjacent the non-elastomeric appliqué to sandwich the appliqué between the elastomeric film and the first nonwoven web. Further steps include positioning a second nonwoven web adjacent a second surface of the elastomeric film and bonding the elastomeric film, the appliqué and the first and second nonwoven webs together to form the multiple layer laminate.

In an embodiment according to this aspect, the first nonwoven may be the inner nonwoven of the absorbent article, that is, the nonwoven that is positioned to contact the body of the wearer. Alternatively, in another embodiment, the first nonwoven may be the outer nonwoven of the absorbent article, that is, the nonwoven that is positioned on the side of the article opposed to the wearer.

Embodiments of the absorbent article also include those in which the indicia is visible through the first nonwoven web, the second nonwoven web, or both of the first and second nonwoven webs. In other words, regardless of the position of the appliqué, the indicia may designed to be visible on the body-side of the article, on the garment-side of the article, or be designed to optionally be visible through each of the body- and garment-sides of the absorbent article.

Optionally, the method may further comprise the step of step of ultrasonically bonding the elastomeric film, the non-elastomeric appliqué and the first and the second non-woven webs together. Other bonding processes may also be suitable for use in the present invention, such as those previously described herein.

Though the manufacturing steps described and claimed herein are optionally performed in the order described or claimed, they can be performed in any order, depending upon the equipment and processes selected and the preferences of the manufacturer. For example, the order of positioning or coupling layers such as the elastomeric film, one or more outer layers, and non-elastomeric appliqués can be performed in a variety of orders.

While the invention includes the various embodiments described above, other embodiments of the invention may also include features as shown and described in U.S. patent application Ser. No. 10/617,218 to Glaug et al., filed on Jul. 10, 2003, Ser. No. 11/236,994 to Babusik et al., filed on Sep. 28, 2005 and Ser. Nos. 11/904,467, 11/904,468 and 11/904,493, all of which were filed on Sep. 27, 2007, which applications are incorporated herein by reference. Each of the embodiments of the present invention is expected to provide equal or better functional performance and customer acceptance at a lower cost as compared to conventional protective undergarments.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A multiple layer laminate having visible indicia for use in an absorbent article, the multiple layer laminate comprising:
a first outer layer;
a second outer layer;
an elastomeric film interposed between said first outer layer and said second outer layer, the elastomeric film being in a stretched condition throughout its extent; and
a non-elastomeric applique having said indicia, said non-elastomeric applique being interposed between said elastomeric film and said first outer layer or between said elastomeric film and said second outer layer, the elastomeric film extending completely and continuously across the appliqué, wherein
said non-elastomeric applique is directly coupled to said elastomeric film such that said non-elastomeric applique prevents retraction of the elastomeric film from the stretched condition, and wherein said indicia is positioned to be visible through said first outer layer, said second outer layer or said first and said second outer layers.

2. The absorbent article of claim 1 wherein said first outer layer, said second outer layer, said elastomeric film and said non-elastomeric applique are coupled together by ultrasonic bonds.

3. The absorbent article of claim 1 wherein said non-elastomeric applique comprises a thermoplastic film material.

4. The absorbent article of claim 3 wherein said non-elastomeric applique comprises a polypropylene or a polyethylene film material.

5. The absorbent article of claim 1 wherein said indicia on said non-elastomeric applique is selected from the group consisting of a printed art graphic, a sewn material, an embroidered material, and a pasted material.

6. The absorbent article of claim 5 wherein said indicia comprises an art graphic printed on said non-elastomeric applique.

7. The absorbent article of claim 1 wherein said first and second outer layers each comprises a nonwoven material.

8. The absorbent article of claim 1 wherein said multiple layer laminate is adapted for use in an absorbent article selected from the group consisting of disposable underwear, briefs, training pants, and sanitary napkins.

9. The absorbent article of claim 1 wherein the elastomeric film is retracted from the stretched condition, and said non-elastomeric applique has a neck-down of about 0% to about 40% when the elastomeric film is retracted from the stretched condition.

10. The absorbent article of claim 9 wherein the elastomeric film is retracted from the stretched condition, and said non-elastomeric applique has a neck-down of about 10% to about 30% when the elastomeric film is retracted from the stretched condition.

11. An absorbent article having visible indicia, the absorbent article comprising:
a multiple layer chassis, at least a portion of which includes:
a first outer layer;
a second outer layer;
an elastomeric film interposed between said first outer layer and said second outer layer, the elastomeric film being in a stretched condition throughout its extent; and
a non-elastomeric applique having said indicia, said non-elastomeric applique being interposed between said elastomeric film and said first outer layer or between said elastomeric film and said second outer layer, the elastomeric film extending completely and continuously across the appliqué, wherein said non-elastomeric applique is directly coupled to said elastomeric film such that said non-elastomeric applique prevents retraction of said elastomeric film from the stretched condition, and wherein said indicia is positioned to be visible through said first outer layer, said second outer layer, or said first and said second outer layers.

12. The absorbent article of claim 11 further comprising an absorbent core.

13. The absorbent article of claim 11 wherein said first outer layer, said second outer layer, said elastomeric film and said non-elastomeric applique are coupled together by ultrasonic bonds.

14. The absorbent article of claim 11 wherein said non-elastomeric applique comprises a thermoplastic film material.

15. The absorbent article of claim 14 wherein said non-elastomeric applique comprises a polypropylene or a polyethylene film material.

16. The absorbent article of claim 11 wherein said indicia on said non-elastomeric applique is selected from the group consisting of a printed art graphic, a sewn material, an embroidered material, and a pasted material.

17. The absorbent article of claim 16 wherein said indicia comprises an art graphic printed on said non-elastomeric applique.

18. The absorbent article of claim 11 wherein said first and second outer layers each comprises a nonwoven material.

19. The absorbent article of claim 11 wherein said absorbent article is selected from the group consisting of disposable underwear, briefs, training pants, and sanitary napkins.

20. The absorbent article of claim 11 wherein the elastomeric film is retracted from the stretched condition and said non-elastomeric applique has a neck-down of about 0% to about 40% when the elastomeric film is retracted from the stretched condition.

21. The absorbent article of claim 20 wherein the elastomeric film is retracted from the stretched condition and said non-elastomeric applique has a neck-down of about 10% to about 30% when the elastomeric film is retracted from the stretched condition.

22. The absorbent article of claim 20 wherein the indicia on said non-elastomeric applique is distorted in the direction of the neck-down in a range of about 0% to about 40%.

23. An absorbent article having visible indicia comprising:
a front panel;
a rear panel; and
a crotch panel extending between said front panel and said rear panel, said crotch panel being associated with an absorbent core;
wherein edges of the front panel are connected to edges of said rear panel to define a waist opening;
said front panel or said rear panel comprising a multiple layer laminate having:
a first outer layer;
a second outer layer;
an elastomeric film interposed between said first outer layer and said second outer layer, the elastomeric film being in a stretched condition throughout its extent; and
a non-elastomeric applique having said indicia, said non-elastomeric applique being interposed between said elastomeric film and said first outer layer or between said elastomeric film and said second outer layer, the elastomeric film extending completely and continuously across the appliqué, wherein said non-elastomeric applique is directly coupled to said elastomeric film, and wherein said indicia is positioned to be visible through said first outer layer or said second outer layer.

24. The absorbent article of claim 23 wherein said non-elastomeric applique limits retraction of said elastomeric film from the stretched condition in a location where said non-elastomeric applique is coupled to said elastomeric film.

25. The absorbent article of claim 23 wherein said indicia on said non-elastomeric applique is selected from the group consisting of a printed art graphic, a sewn material, an embroidered material, and a pasted material.

26. The absorbent article of claim 25 wherein said non-elastomeric applique comprises an art graphic printed on said non-elastomeric applique.

* * * * *